United States Patent
Rosenblood

(10) Patent No.: US 10,307,083 B2
(45) Date of Patent: *Jun. 4, 2019

(54) POSTURE AND DEEP BREATHING IMPROVEMENT DEVICE, SYSTEM, AND METHOD

(71) Applicant: Kenneth Lawrence Rosenblood, Los Angeles, CA (US)

(72) Inventor: Kenneth Lawrence Rosenblood, Los Angeles, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/055,621

(22) Filed: Aug. 6, 2018

(65) Prior Publication Data

US 2018/0344214 A1 Dec. 6, 2018

Related U.S. Application Data

(60) Continuation of application No. 15/914,136, filed on Mar. 7, 2018, now Pat. No. 10,064,572, which is a
(Continued)

(51) Int. Cl.
*A61B 5/11* (2006.01)
*A61B 5/00* (2006.01)
*A61B 5/103* (2006.01)

(52) U.S. Cl.
CPC ............ *A61B 5/1116* (2013.01); *A61B 5/103* (2013.01); *A61B 5/486* (2013.01); *A61B 5/4836* (2013.01); *A61B 5/74* (2013.01)

(58) Field of Classification Search
CPC ....... A61B 5/103; A61B 5/1116; A61B 5/486; A61B 5/74
(Continued)

(56) References Cited

U.S. PATENT DOCUMENTS 5,333,106 A * 7/1994 Lanpher .................. G09B 5/02
128/200.12
5,511,854 A * 4/1996 Cordia .................. A61F 5/3707
297/393
(Continued)

*Primary Examiner* — Ojiako K Nwugo
(74) *Attorney, Agent, or Firm* — Hankin Patent Law, APC; Kevin Schraven; Anooj Patel

(57) ABSTRACT

A posture and breathing improvement device, system, and method. The system for improving posture and deep breathing may comprise: a sensor device; posture/breathing improvement software program, comprising one, both, or a combination of a posture improvement system interface and a breathing improvement system interface; and one or more user devices. The sensor device may be physically associated with a user and may communicate with the posture improvement software program. The sensor device may comprise: one or more sensors for monitoring positions and movements of the user. The system may calculate one or more optimum postural positions and breathing exercises for the user, based on data communicated by the sensor device and collected information about the user. The system may monitor a conformance of the user with the optimum postural positions and may display the conformance on the posture improvement system interface. The system may detect and notify the user of one or more non-conformances, such that a user is reminded to maintain at least one optimum postural position and periodically take deep breaths.

13 Claims, 18 Drawing Sheets

Related U.S. Application Data continuation-in-part of application No. 15/676,137, filed on Aug. 14, 2017, which is a division of application No. 14/918,334, filed on Oct. 20, 2015, now Pat. No. 9,763,603.

(60) Provisional application No. 62/066,800, filed on Oct. 21, 2014.

(58) Field of Classification Search
USPC .......................... 340/573.1, 573.7; 600/301
See application file for complete search history.

(56) References Cited

U.S. PATENT DOCUMENTS

| | | | |
|---|---|---|---|
| 9,265,681 B1* | 2/2016 | Bell | A61G 7/07 |
| 2007/0149360 A1* | 6/2007 | Narayanaswami | A63B 24/00 482/8 |
| 2009/0324024 A1* | 12/2009 | Worthington | A61B 5/103 382/118 |
| 2010/0274100 A1* | 10/2010 | Behar | A61B 5/0002 600/301 |
| 2011/0087115 A1* | 4/2011 | Sackner | A61B 5/0205 600/484 |
| 2011/0275939 A1* | 11/2011 | Walsh | A61B 5/4561 600/473 |
| 2013/0144111 A1* | 6/2013 | Wang | A61M 21/02 600/27 |
| 2013/0207889 A1* | 8/2013 | Chang | A61B 5/0002 345/156 |
| 2014/0019080 A1* | 1/2014 | Chan | G01P 21/00 702/104 |
| 2014/0129178 A1* | 5/2014 | Meduna | G06F 17/00 702/189 |
| 2014/0302472 A1* | 10/2014 | Fletcher | G09B 19/00 434/262 |
| 2014/0318699 A1* | 10/2014 | Longinotti-Buitoni | A61B 5/0002 156/247 |
| 2015/0065919 A1* | 3/2015 | Cuevas | A61B 5/1116 600/587 |
| 2015/0342518 A1* | 12/2015 | Persidsky | A61B 5/486 600/534 |
| 2017/0246071 A1* | 8/2017 | Schultz | A41D 13/1236 |
| 2017/0358239 A1* | 12/2017 | Arney | A61B 5/0816 |
| 2018/0125392 A1* | 5/2018 | Aslam | A61M 15/0086 |

* cited by examiner

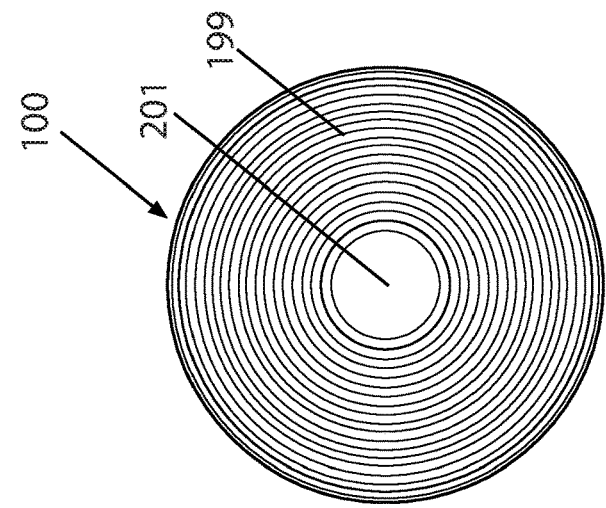
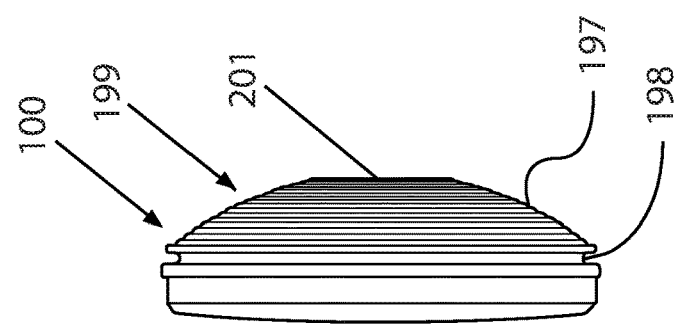
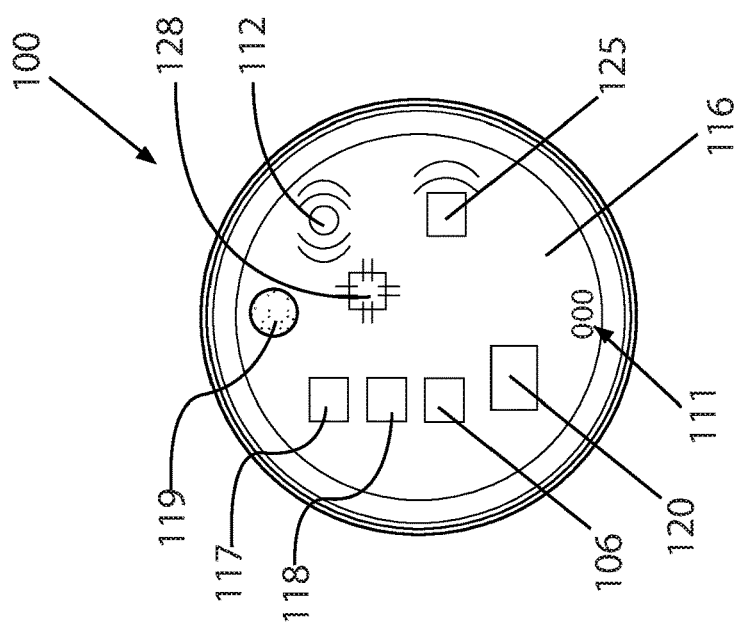

POSTURE AND DEEP BREATHING IMPROVEMENT DEVICE, SYSTEM, AND METHOD

CROSS REFERENCE TO RELATED APPLICATIONS

This application is a Continuation of U.S. Non-Provisional patent application Ser. No. 15/914,136, now U.S. Pat. No. 10,064,572, filed on Mar. 7, 2018, entitled "POSTURE AND DEEP BREATHING IMPROVEMENT DEVICE, SYSTEM, AND METHOD", which is a Continuation in Part of U.S. Non-Provisional patent application Ser. No. 15/676,137, filed on Aug. 14, 2017, entitled "POSTURE IMPROVEMENT DEVICE, SYSTEM, AND METHOD", which is a Divisional Application of U.S. Non-Provisional patent application Ser. No. 14/918,334, now U.S. Pat. No. 9,763,603, filed on Oct. 20, 2015, entitled "POSTURE IMPROVEMENT DEVICE, SYSTEM, AND METHOD", which claims benefit of U.S. Provisional Patent Application No. 62/066,800 filed on Oct. 21, 2014, entitled "POSTURE IMPROVEMENT DEVICE", the contents of all of which are incorporated herein by this reference as though set forth in their entirety, and to which priority and benefit are claimed.

FIELD OF USE

The present disclosure relates generally to systems for improving posture and deep breathing, and more particularly, to systems that conditions a user to practice improved posture and deep breathing through real-time viewing monitoring of their own posture, warnings, reminders to exercise and stretch programs, and behavioral modification.

BACKGROUND

There is a strong correlation between good posture and good health. Many productive hours are lost each year due to pain and sickness associated with posture-induced health issues. Improved posture has been shown to increase levels of dopamine and testosterone produced by the brain, and research has indicated that correction of postural kyphosis in patients with ADHD may lead to a significant reduction of ADHD symptoms. When people operate with good posture, research indicates that performance regarding mental acuity, self-esteem, and physiological efficiency is improved. Thus, providing insight and a mechanism for improving posture has been a desirable goal for many people as it improves mental performance and overall health.

Breathing, like posture, is also important to health. The way humans breathe can impact their whole body. Breathing helps regulate important bodily functions such as heart rate and blood pressure, as well as reinforcing proper body mechanics that put less stress and strain on the body during movements. Deep breathing is associated with better health. Many people are too busy and too sedentary, which has conditioned many to take only take quick, shallow breaths. Over time, this weakens respiratory muscles and can create tension in the upper body. This can change a person's posture and undermine his/her health. Regular physical activity and sessions of respiratory muscle training can reverse problems caused by shallow breathing.

People inhale and exhale air by active contractions of the respiratory muscles that surround a person's lungs. During inhalation, the diaphragm contracts to create space in the chest cavity for the lungs to expand. The intercostal muscles, located between the ribs, assist the diaphragm by elevating the rib cage to allow more air to be taken into the lungs. Additional muscles around the neck and upper chest assist the intercostals if breathing becomes impaired. These additional muscles, which include the sternocleidomastoid, serratus anterior, pectoralis minor, and scalene, act to increase the speed and quantity of movement of the chest.

Breathing from the chest relies primarily on the additional muscles around the neck and collarbone, rather than relying on the diaphragm. When chest breathing is accompanied by poor posture, many muscles in the upper body lose their ability to properly function. The longer a person sits during the day, the less our body is able to fight the forces of gravity and maintain a strong, stable core. Tight accessory muscles around the chest, in particular the pectoralis minor and scalene, may cause rounded shoulders and improper head posture. This may weaken the back muscles by inhibiting the normal use of latissimus dorsi, middle trapezius, and rhomboids, and quadratus lumborum, which are necessary to maintain proper and upright posture.

There are many benefits to deep breathing, which as providing a sense of calm, reducing stress and anxiety, and lowering blood pressure. Deep breathing is the basis for many meditative and mindfulness practices. Thus, deep breathing is very important to a healthy mind and body.

Although wearable devices may remind the wearer to take deep breaths, none of these devices, before the device of the present disclosure, provide a kinetic display that compares a user's actual breathing to an optimal breathing pattern in a gamification manner. Additionally, breathing devices before the device of the present disclosure are not combined with a posture device, wherein the posture device has a copper coil that provides induction charging and protection from and direction of radio waves.

Therefore, there is a need for a device, system, and method that can improve posture and provide a kinetic display that compares a user's actual breathing to an optimal breathing pattern in a gamification manner. Additionally, what is needed is a posture and/or breathing improvement device that has a copper coil that provides induction charging and protection from and direction of radio waves.

SUMMARY OF EMBODIMENTS

To minimize the limitations in the prior art, and to minimize other limitations that will become apparent upon reading and understanding the present disclosure, the present specification discloses a new and improved device, system, and method for improving posture and deep breathing.

One embodiment may be a system for improving posture and deep breathing, comprising: a sensor device; a posture and breathing improvement software program that may be configured to run on one or more user devices; wherein the posture and breathing improvement software program may comprise a breathing kinetic graphical user interface; wherein the breathing kinetic graphical user interface may be displayed on the one or more user devices; wherein the breathing kinetic graphical user interface may comprise an optimal breath inhale graphic and an actual dynamic kinetic breathing graphic; wherein the actual dynamic kinetic breathing graphic expands and contracts, such that a user may be able to visually monitor diaphragmatic breathing; wherein the sensor device comprises: one or more sensors; a wireless communication device; and a housing; wherein the sensor device may be configured to be placed in proximity to a user; wherein the wireless communication device may be configured to communicate with the one or more user devices, such that the sensor device may be in communication with the posture and breathing improvement software program; wherein the one or more sensors may detect and measure one or more movements by the user to create a plurality of sensor data; wherein the wireless communication device may transmit the plurality of sensor data to the one or more user devices; and wherein the detection, measurement, and transmission of the plurality of sensor data may allow the one or more user devices to allow the user to monitor their diaphragmatic breathing. The actual dynamic kinetic breathing graphic and the optimal breath inhale graphic may be, respectively, a dilating dot and a circle. The optimal breath inhale graphic may be an expansion goal for the actual dynamic kinetic breathing graphic. The optimal breath inhale graphic may be a dynamic expansion goal for the actual dynamic kinetic breathing graphic. The optimal breath inhale graphic may be a dynamic kinetic circle that dilates and may be a goal that the user tries to matingly follow via the actual dynamic kinetic breathing graphic. The detection, measurement, and transmission of the plurality of sensor data allows the one or more user devices to allow the user to monitor their diaphragmatic breathing. The housing may comprise a copper coil, wherein the copper coil may be configured to allow the sensor device to be wirelessly recharged. The copper coil may be configured to a) shield the user from electromagnetic radiation generated by the sensor device and b) direct wireless communications away from the user. The housing may comprise a concave slope. The posture and breathing improvement software program may further comprise a posture improvement system interface; wherein the posture improvement system interface may be displayed to the user on the one or more user devices; wherein the posture improvement software program may be configured to collect information about the user; wherein the posture and breathing improvement software program calculates one or more optimum postural positions for the user, based on data communicated by the sensor device and the collected information about the user. The posture and breathing improvement software program may monitor a conformance of the user with at least one of the one or more optimum postural positions; wherein the posture improvement system interface may be configured to display the conformance; and wherein the posture and breathing improvement software program detects and notifies the user of one or more non-conformances, such that a user may be reminded to maintain the at least one of the one or more optimum postural positions. The displaying of the conformance of the user with at least one of the one or more optimum postural positions may be illustrated via a pictograph target and a target ball. The posture target ball may be substantially within a center of the target when the user may be in the conformance with the at least one of the one or more optimum postural positions. When the user fails to maintain the at least one of the one or more optimum postural positions, the posture target ball may be not substantially within the center of the target and the posture improvement system interface may notify the user of the one or more non-conformances. When the user fails to maintain the at least one of the one or more optimum postural positions, the user device may be substantially disabled until the user corrects the non-conformance. The system may further comprise a memory unit; wherein the memory unit stores the plurality of sensor data. The one or more sensors may comprise: one or more accelerometers and one or more gyroscopes. The one or more accelerometers may comprise three tri-axial accelerometers and the one or more gyroscopes may comprise three tri-axial rate gyroscopes.

Another embodiment may be a system for improving posture and deep breathing, comprising: a sensor device; a posture and breathing improvement software program that may be configured to run on one or more user devices; wherein the posture and breathing improvement software program may comprise a breathing kinetic graphical user interface and a posture improvement system interface; wherein the breathing kinetic graphical user interface may be displayed on the one or more user devices; wherein the breathing kinetic graphical user interface may comprise an optimal breath inhale graphic and an actual dynamic kinetic breathing graphic; wherein the actual dynamic kinetic breathing graphic may expand and contract, such that a user may be able to monitor diaphragmatic breathing; wherein the posture improvement system interface may be displayed to the user on the one or more user devices; wherein the sensor device may comprise: one or more sensors; a wireless communication device; and a housing; wherein the housing may comprise a copper coil; wherein the copper coil may allow the sensor device to be wirelessly recharged; wherein the copper coil may be configured to shield the user from electromagnetic radiation generated by the sensor device; wherein the copper coil may direct wireless communications away from the user; wherein the sensor device may be configured to be placed in proximity to a user; wherein the wireless communication device may be configured to communicate with the one or more user devices, such that the sensor device may be in communication with the posture and breathing improvement software program; wherein the one or more sensors may detect and measure one or more movements by the user to create a plurality of sensor data; wherein the wireless communication device may transmit the plurality of sensor data to the one or more user devices; wherein the detection, measurement, and transmission of the plurality of sensor data may allow the one or more user devices to allow the user to monitor their diaphragmatic breathing; wherein the posture improvement software program may be configured to collect information about the user; wherein the posture and breathing improvement software program may calculate one or more optimum postural positions for the user, based on data communicated by the sensor device and the collected information about the user; wherein the posture and breathing improvement software program may monitor a conformance of the user with at least one of the one or more optimum postural positions; wherein the posture improvement system interface may be configured to display the conformance; and wherein the posture and breathing improvement software program may detect and notify the user of one or more non-conformances, such that a user may be reminded to maintain the at least one of the one or more optimum postural positions. The housing may comprise a concave slope.

These, as well as other components, steps, features, objects, benefits, and advantages, will now become clear from a review of the following detailed description of illustrative embodiments, of the accompanying drawings, and of the claims.

BRIEF DESCRIPTION OF THE ILLUSTRATIVE EMBODIMENTS

The drawings show illustrative embodiments, but do not depict all embodiments. Other embodiments may be used in addition to or instead of the illustrative embodiments. Details that may be apparent or unnecessary may be omitted for the purpose of saving space or for more effective illustrations. Some embodiments may be practiced with additional components or steps and/or without some or all components or steps provided in the illustrations. When different drawings contain the same numeral, that numeral refers to the same or similar components or steps.

FIG. 1 is an illustration of a front view of one embodiment of the sensor device for improving posture and deep breathing.

FIG. 2 is an illustration of a side view of one embodiment of the sensor device.

FIG. 3 is an illustration of a rear view of one embodiment of the sensor device.

Figure 4A:
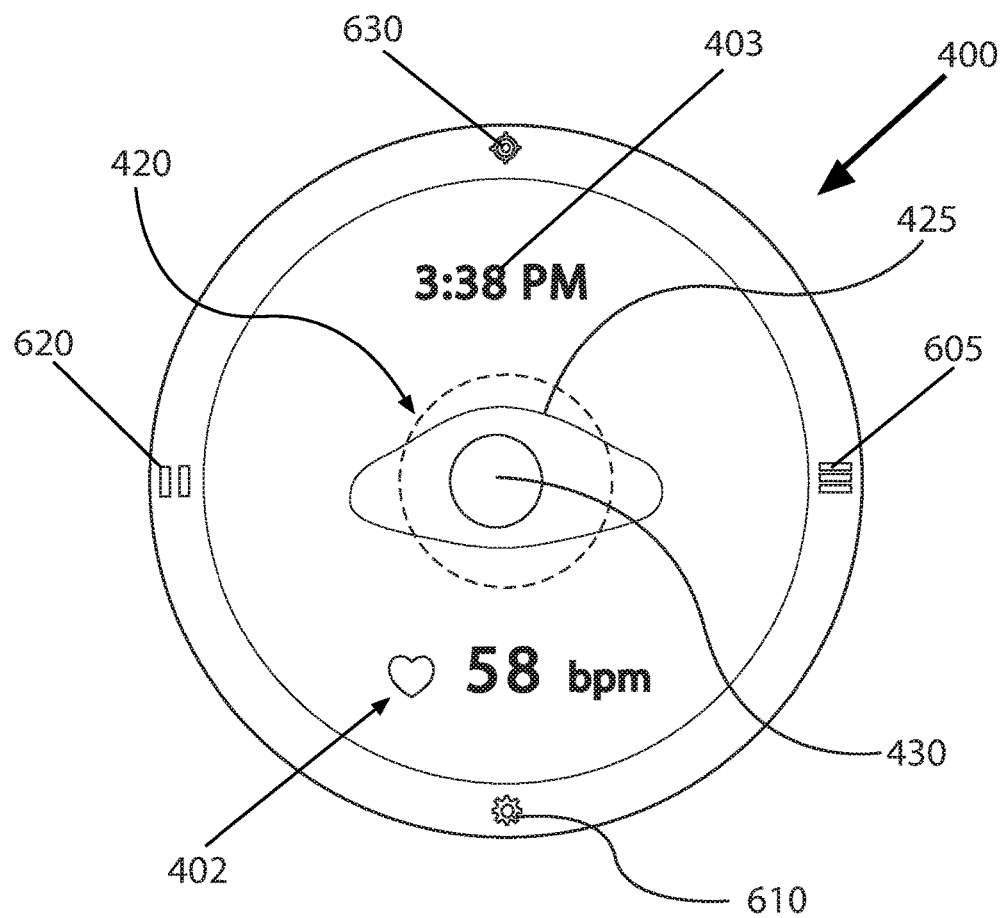
Figure 4B:
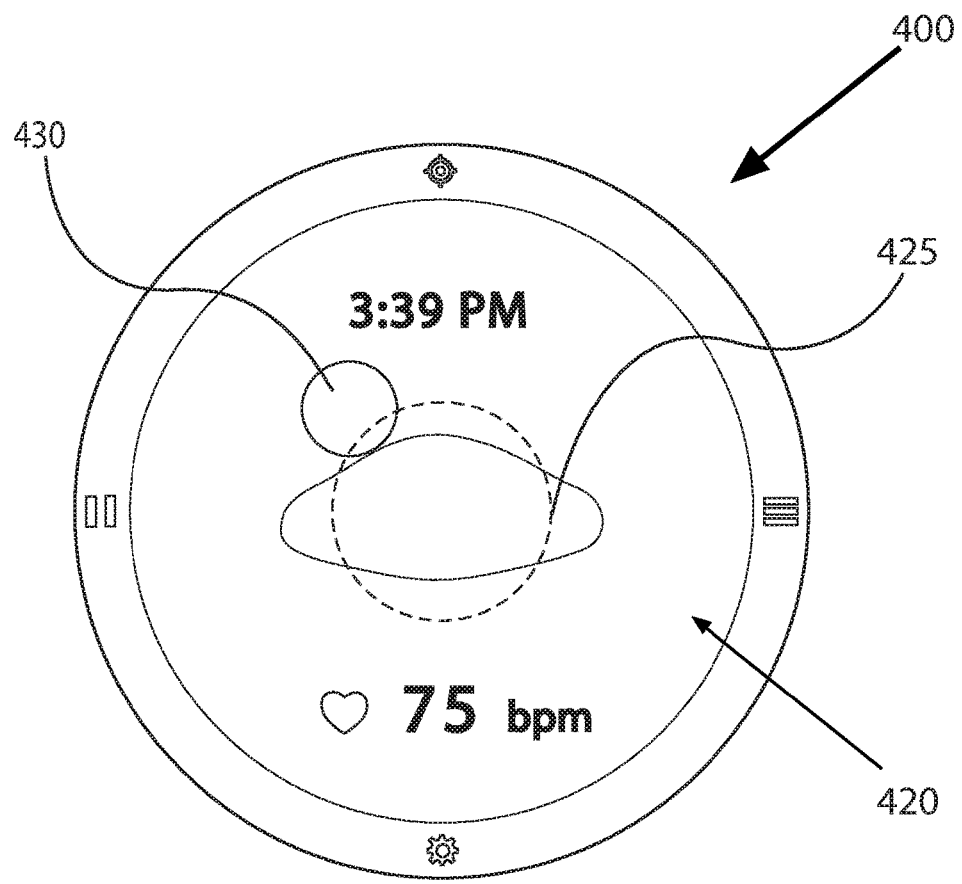
Figure 4C:
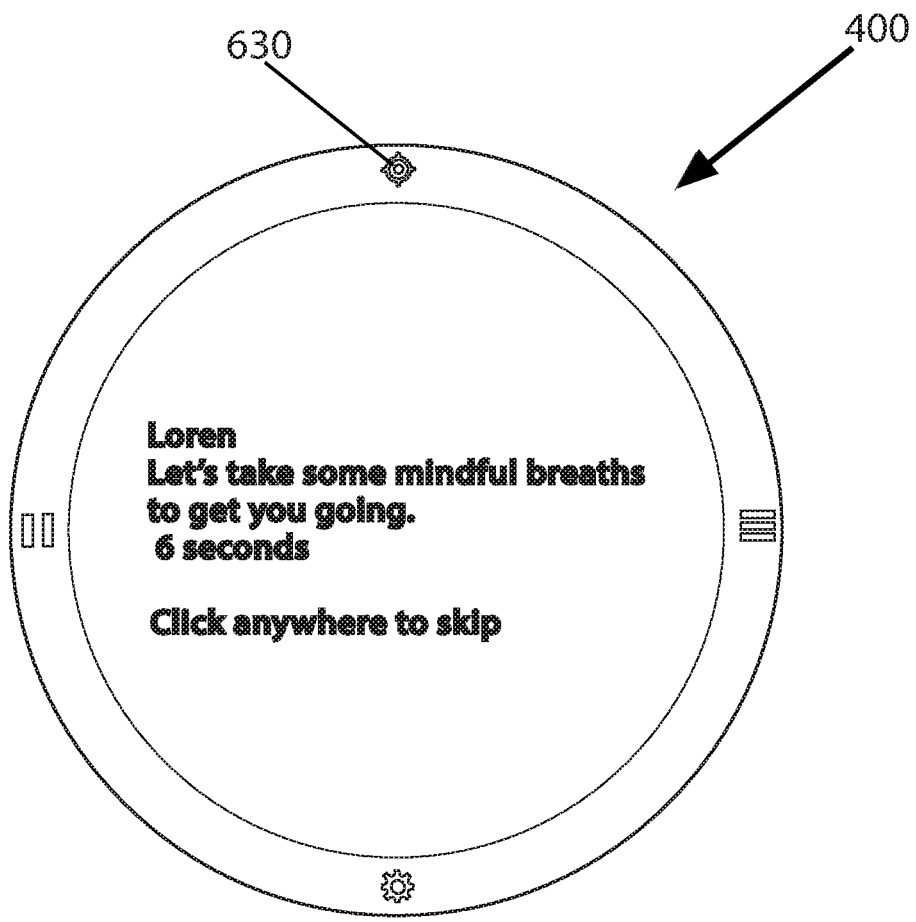

FIGS. 4A-C are illustrations of one embodiment of the posture and deep breathing improvement system interface.

Figure 5:
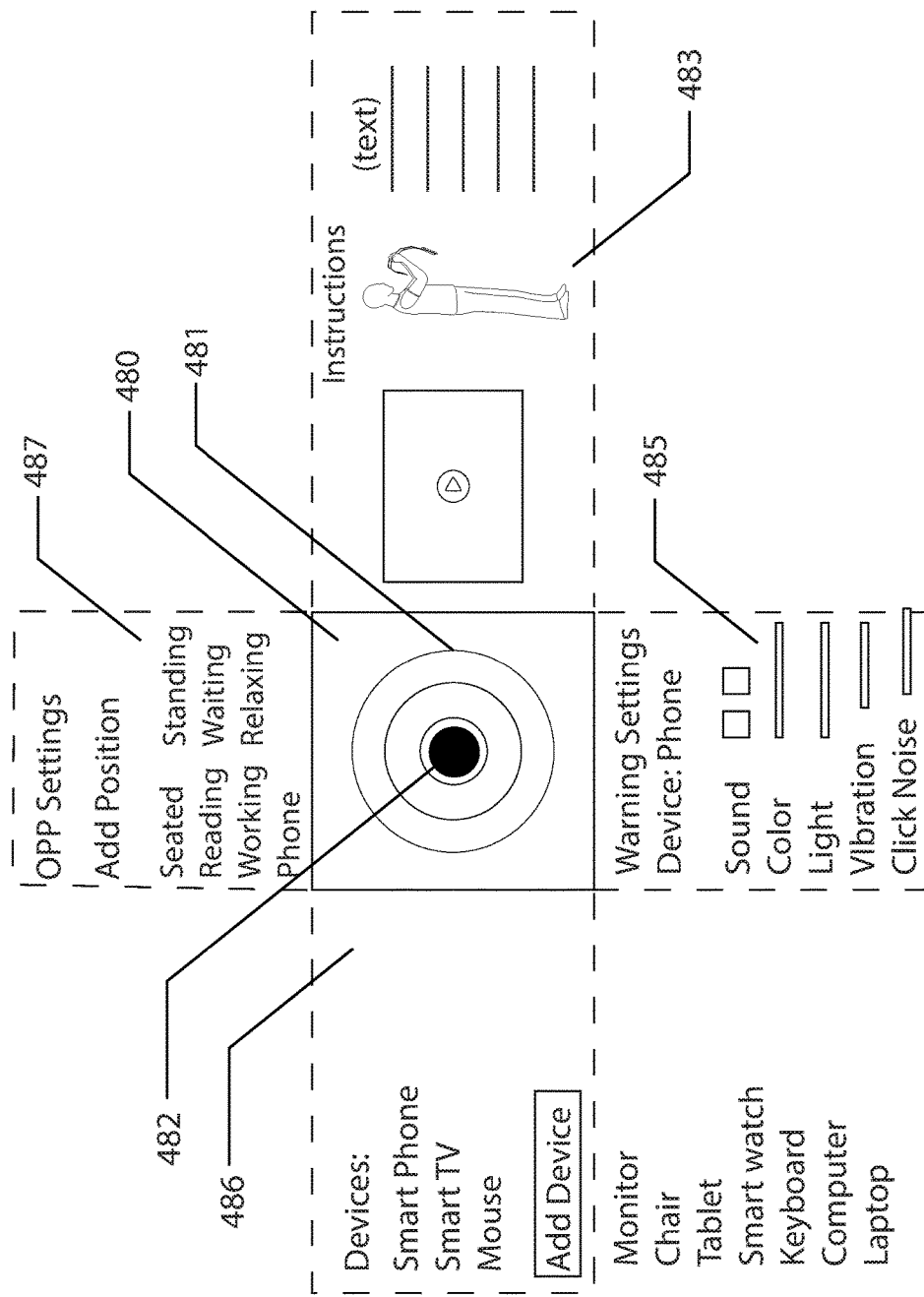

FIG. 5 is an illustration of one embodiment of deep breathing dynamic interface.

Figure 6:
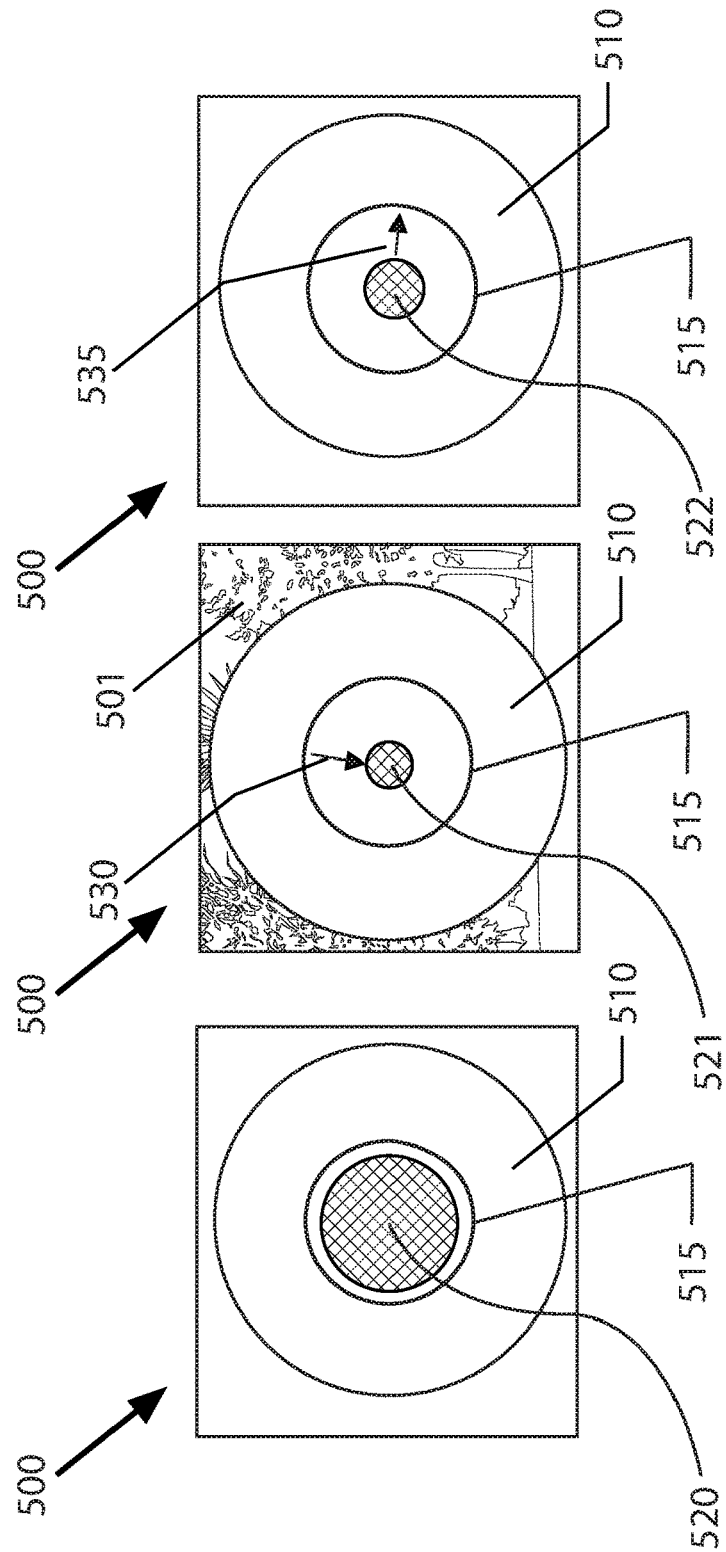

FIGS. 6A-C are illustrations of one embodiment of the posture and deep breathing improvement system interface.

Figure 7:
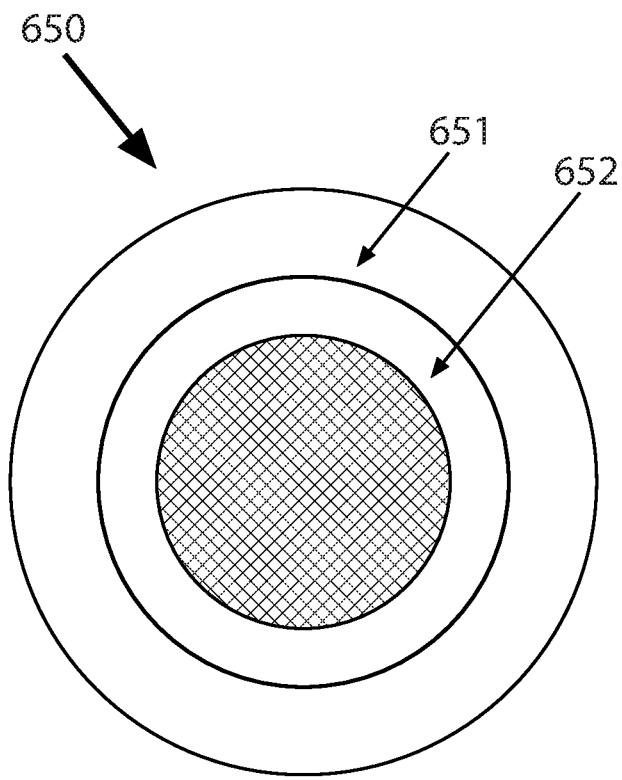

FIG. 7 is an illustration of another embodiment of the posture and deep breathing improvement system interface.

Figure 8:
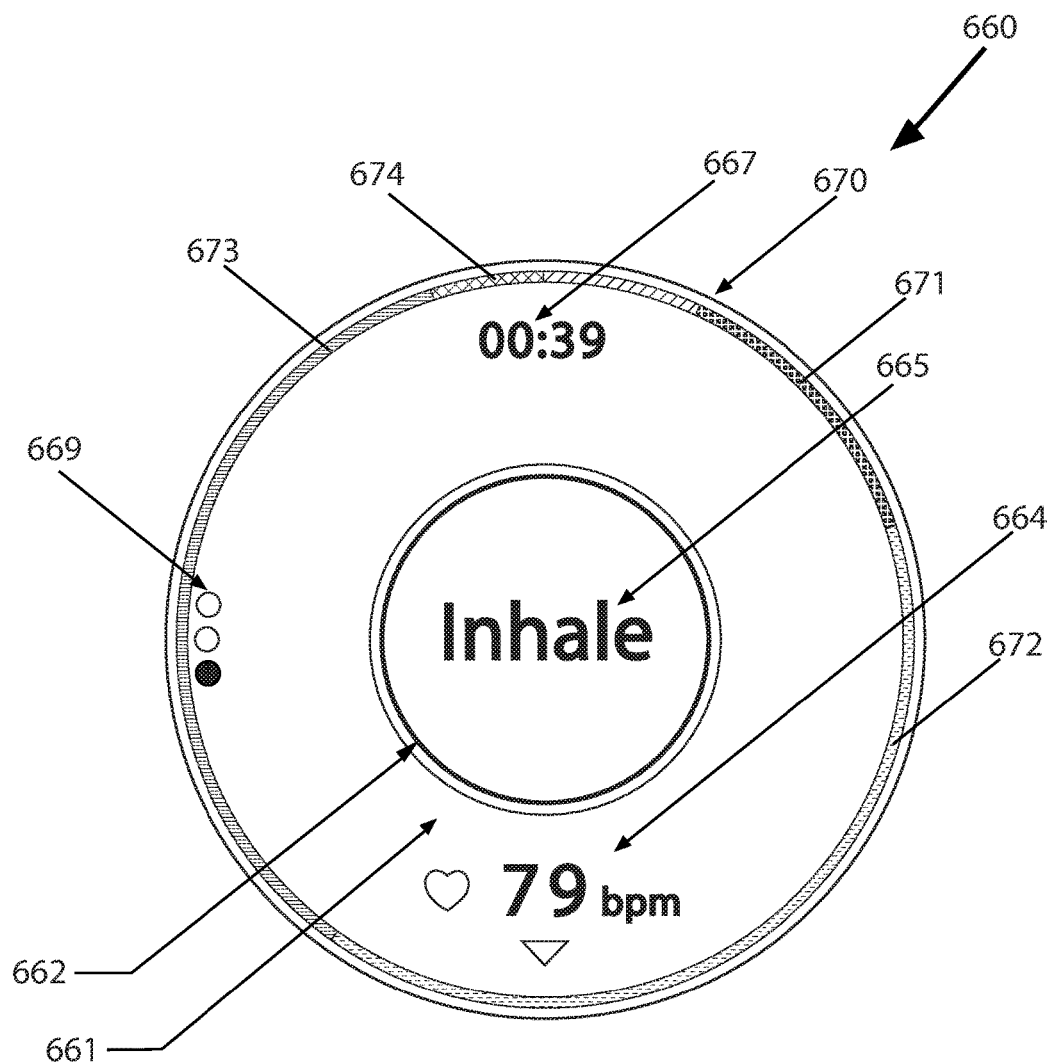

FIG. 8 is an illustration of another embodiment of the posture and deep breathing improvement system interface.

Figure 9:
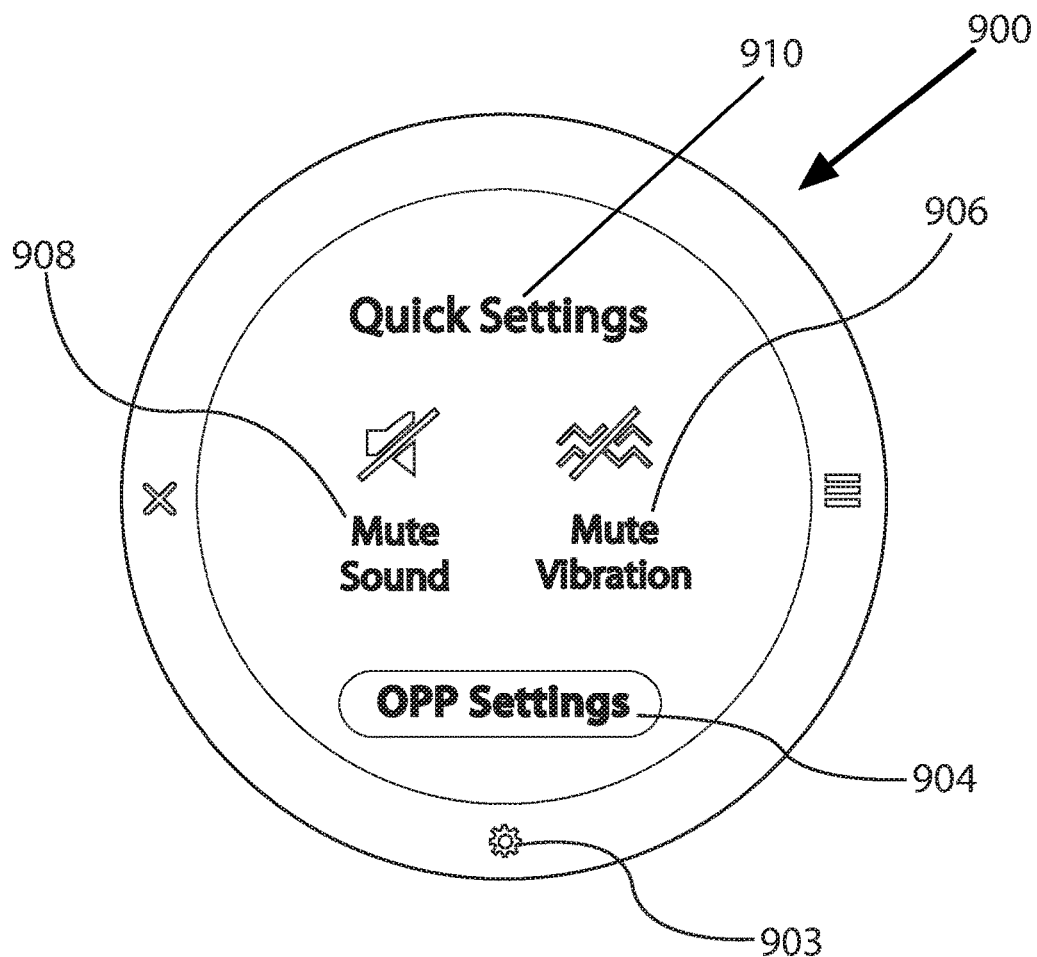

FIG. 9 is an illustration of another embodiment of the posture and deep breathing improvement system interface and shows the settings screen.

Figure 10:
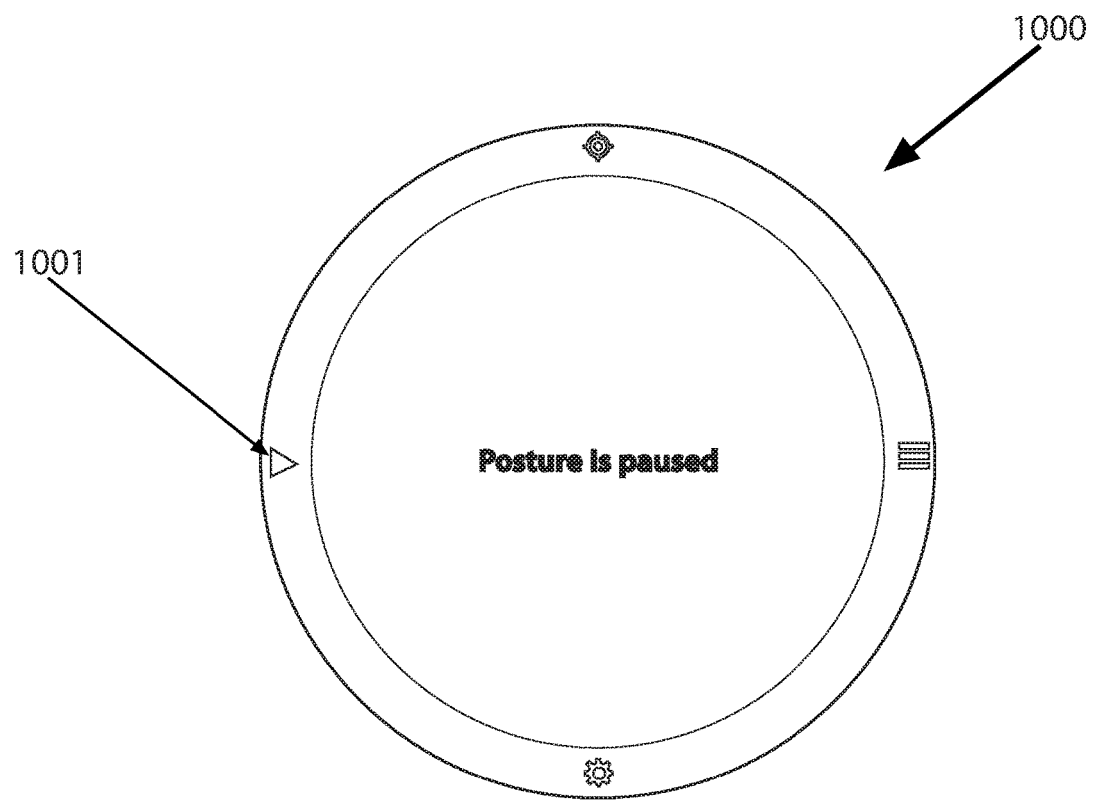

FIG. 10 is an illustration of another embodiment of the posture and deep breathing improvement system interface and shows the pause screen.

Figure 11:
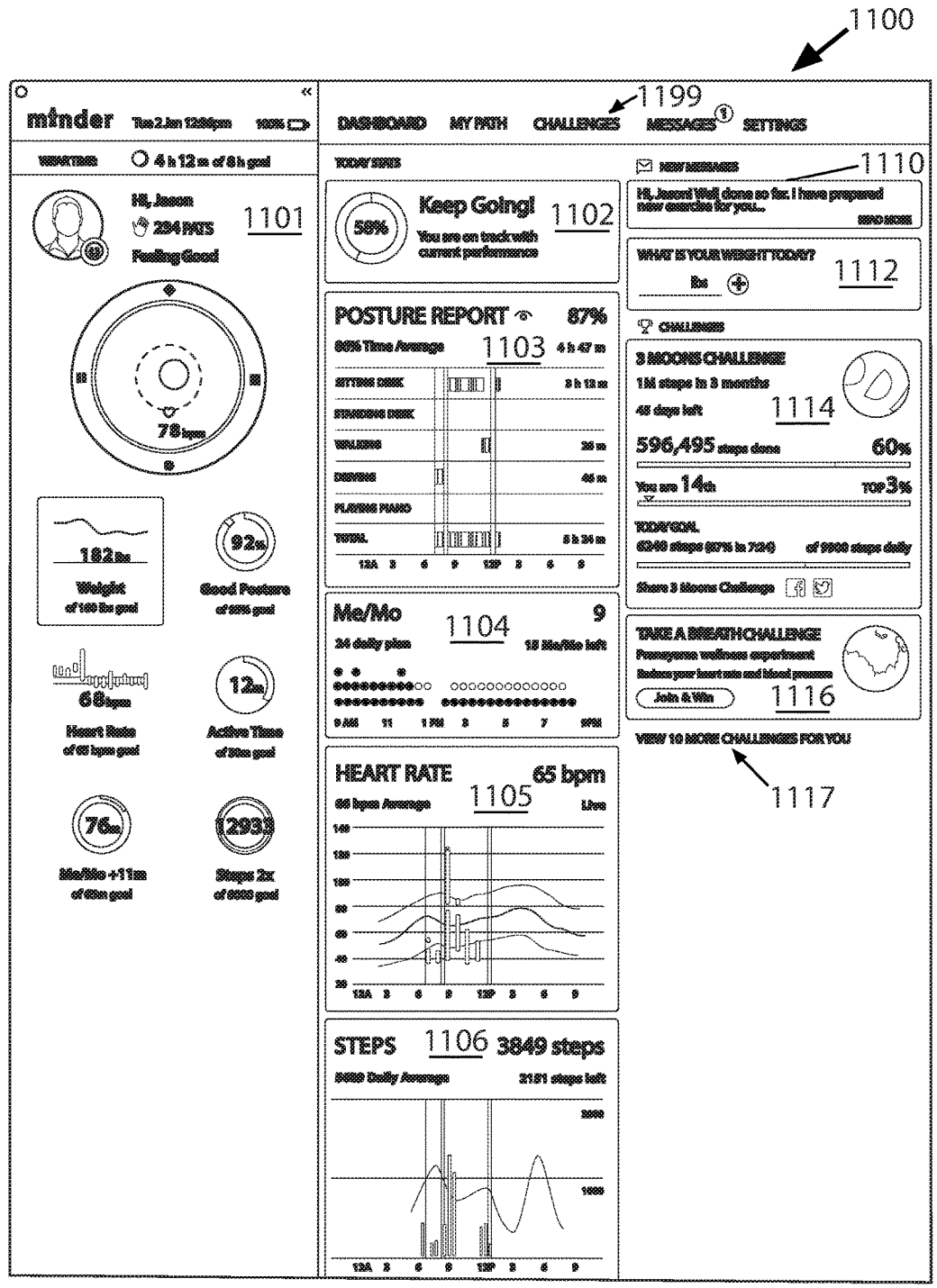

FIG. 11 is an illustration of another embodiment of the posture and deep breathing improvement system interface and shows the dashboard screen.

Figure 12:
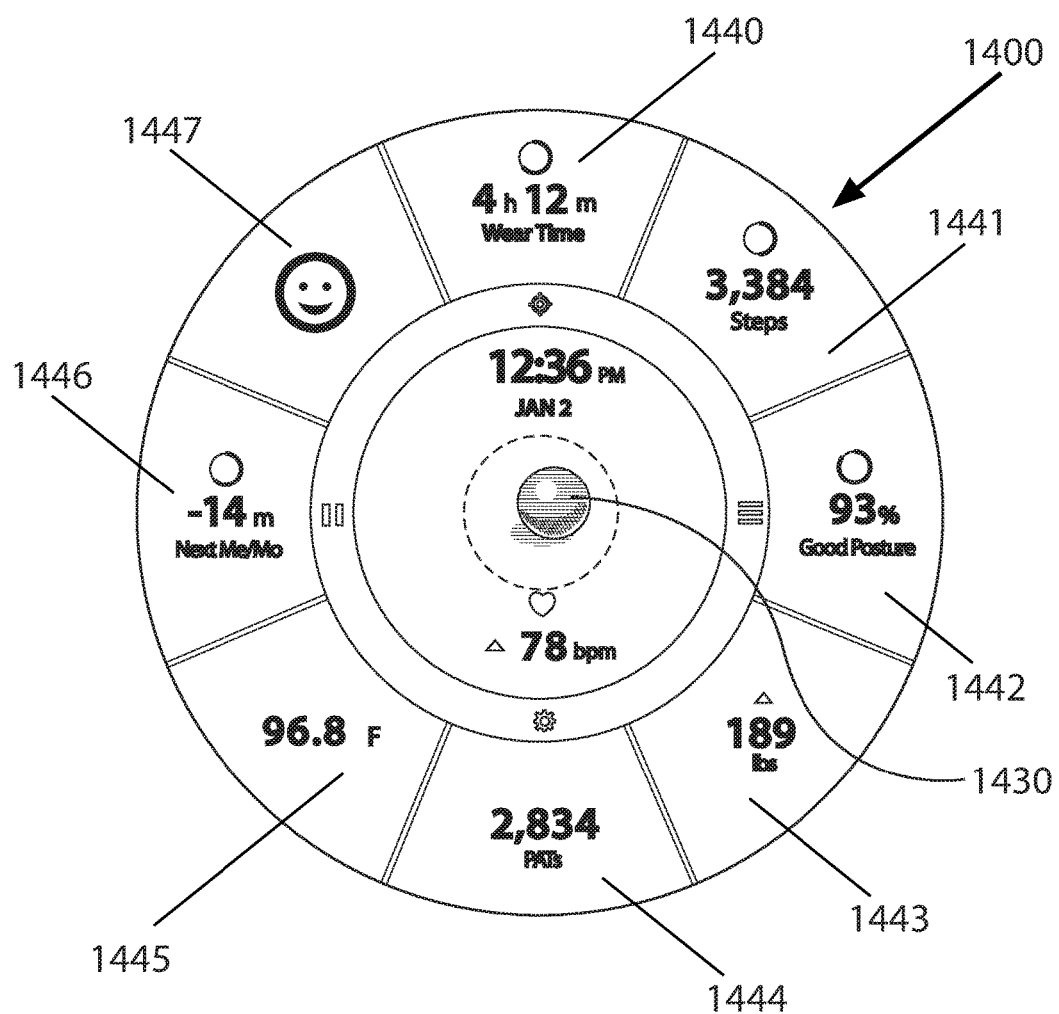

FIG. 12 is an illustration of another embodiment of the posture and deep breathing improvement system interface and shows the HUD screen.

Figure 13:
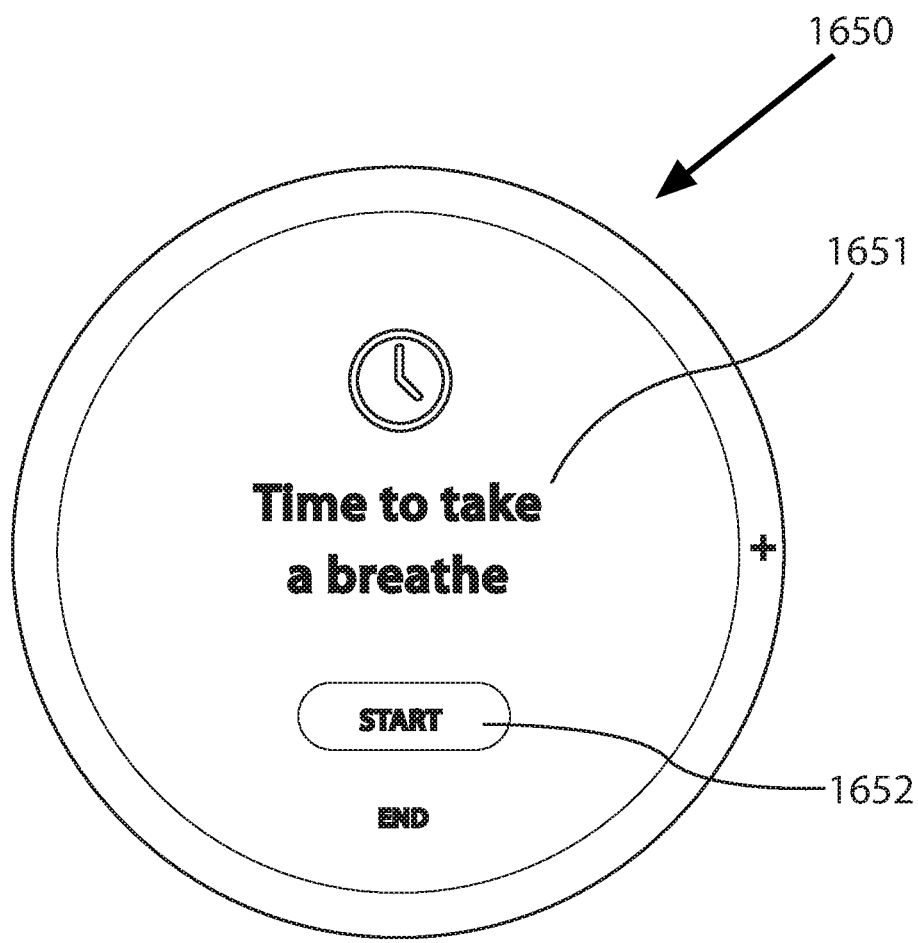

FIG. 13 is an illustration of another embodiment of the posture and deep breathing improvement system interface and shows the Me/Mo screen.

Figure 14:
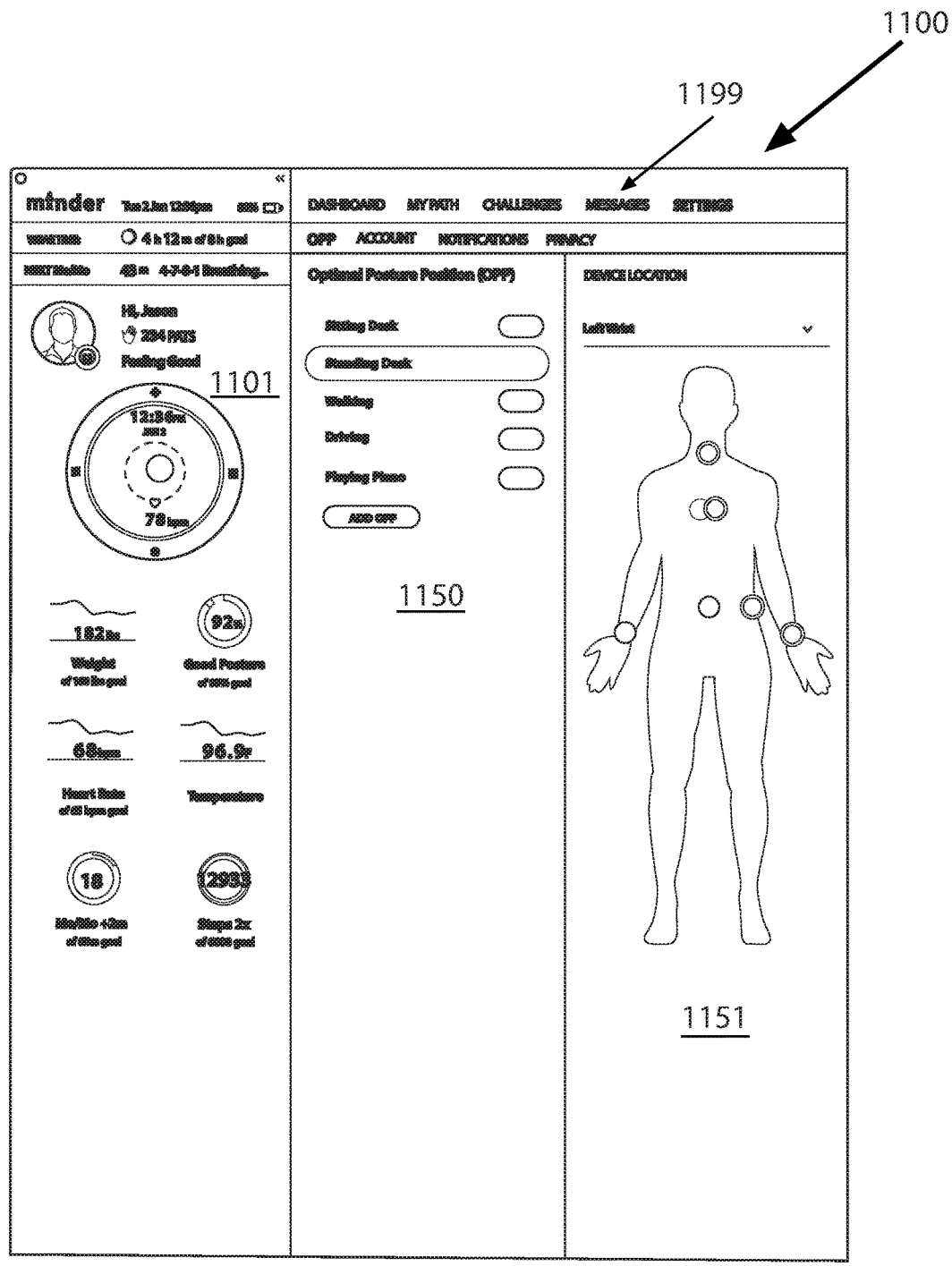

FIG. 14 is an illustration of another embodiment of the posture and deep breathing improvement system interface and shows the dashboard settings screen.

Figure 15:
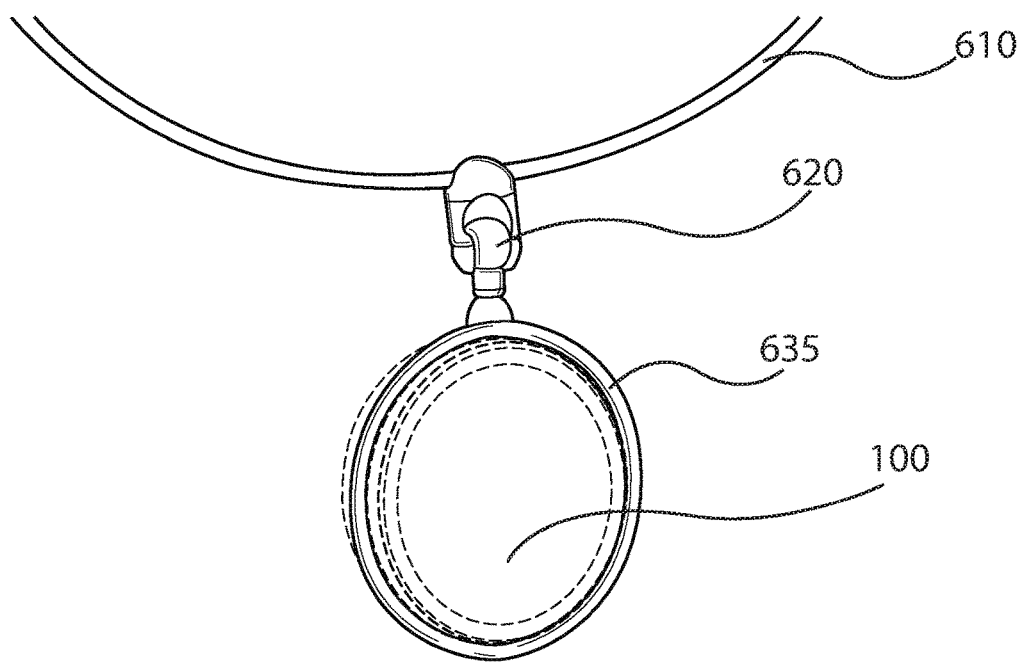

FIG. 15 is an illustration of one embodiment of a holder and harness for the sensor device.

Figure 16:
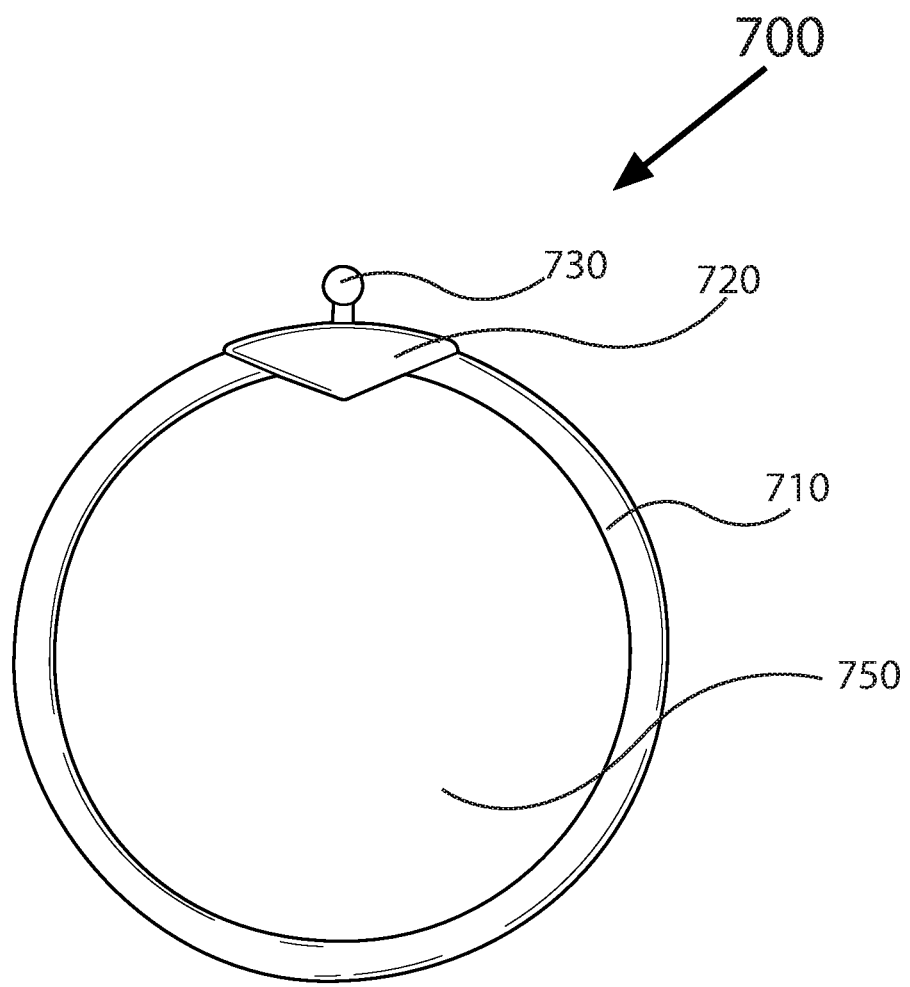

FIG. 16 is an illustration of one embodiment of a holder for the sensor device.

Figure 17:
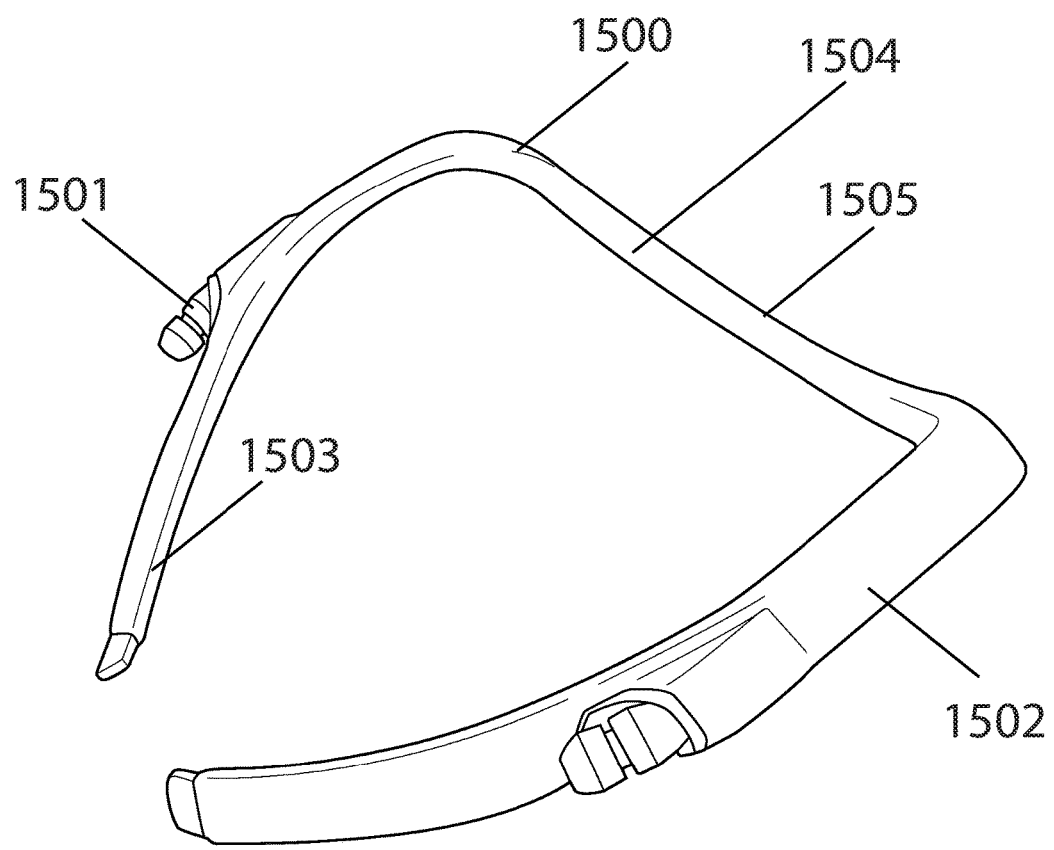

FIG. 17 is an illustration of one embodiment of a poseable harness.

Figure 18:
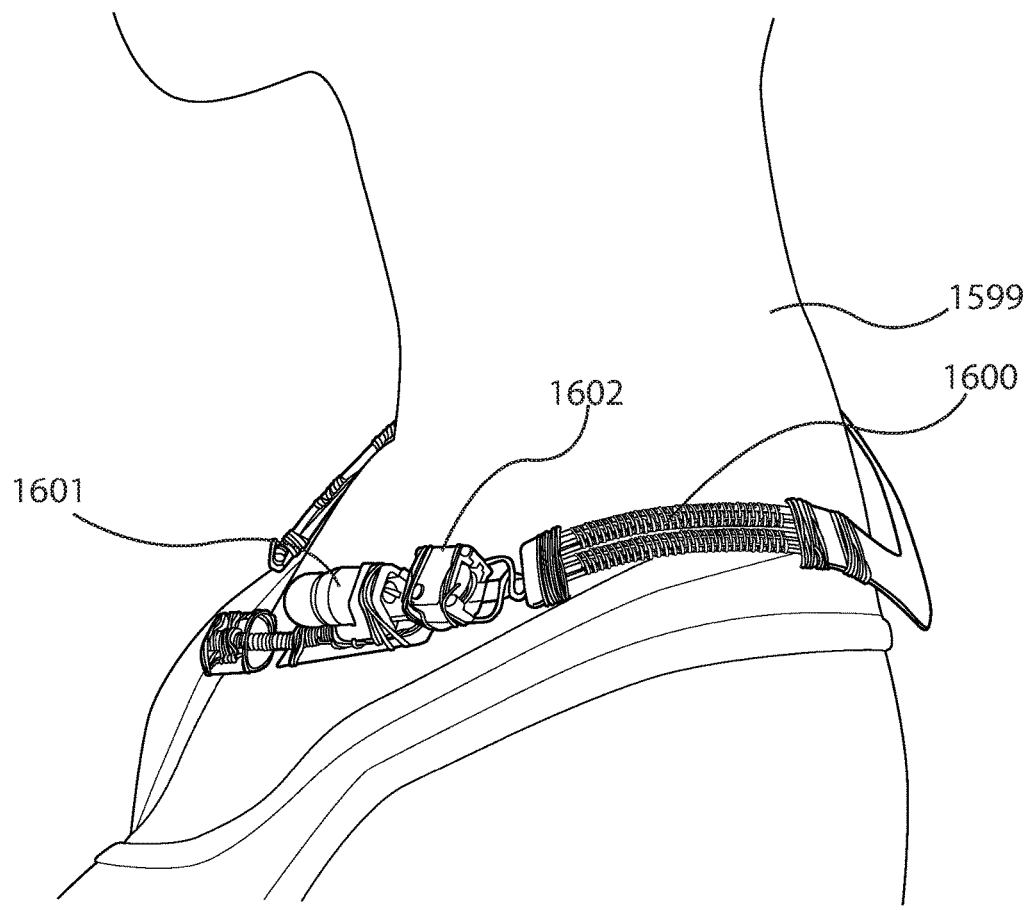

FIG. 18 is an illustration of one embodiment of a poseable harness showing retractable headphones.

DETAILED DESCRIPTION OF THE ILLUSTRATIVE EMBODIMENTS

In the following detailed description, numerous specific details are set forth in order to provide a thorough understanding of various aspects of one or more embodiments. However, the one or more embodiments may be practiced without some or all of these specific details. In other instances, well-known procedures and/or components have not been described in detail so as not to unnecessarily obscure aspects of the embodiments.

While some embodiments are disclosed herein, still other embodiments will become obvious to those skilled in the art as a result of the following detailed description. These embodiments are capable of modifications of various obvious aspects, all without departing from the spirit and scope of protection. The Figures, and their detailed descriptions, are to be regarded as illustrative in nature and not restrictive. Also, the reference or non-reference to a particular embodiment shall not be interpreted to limit the scope of protection.

Definitions

In the following description, certain terminology is used to describe certain features of one or more embodiments. For example, as used herein, the terms "computer", "computing device", or "computer system" refer to any device or machine that processes data or information with an integrated circuit chip, including without limitation, personal computers, mainframe computers, workstations, testing equipment, servers, desktop computers, portable computers, laptop computers, embedded computers, wireless devices including cellular phones, personal digital assistants, tablets, tablet computers, smartphones, portable game players, and hand-held computers. Computing devices may also include mobile computing devices such as smartphones, tablets, wearables, and the like.

As used herein, the term "Internet" generally refers to any collection of networks that utilizes standard protocols, whether Ethernet, Token ring, Wi-Fi, asynchronous transfer mode (ATM), Fiber Distributed Data Interface (FDDI), code division multiple access (CDMA), global systems for mobile communications (GSM), long term evolution (LTE), or any combination thereof. The term "website" refers to any document written in a mark-up language including, but not limited to, hypertext mark-up language (HTML) or virtual reality modeling language (VRML), dynamic HTML, extended mark-up language (XML), wireless markup language (WML), or any other computer languages related thereto, as well as to any collection of such documents reachable through one specific Internet Protocol Address or at one specific World Wide Web site, or any document obtainable through any particular Uniform Resource Locator (URL).

The terms "application", "software", "software application", or "posture improvement software program" generally refer to any set of machine-readable instructions on a client machine, web interface, and/or computer system, that directs a computer's processor to perform specific steps, processes, or operations disclosed herein. The "application", "software", "software application", and "posture improvement software program" may comprise one or more modules that direct the operation of the computing device or computer system for monitoring a conformance of the user with one or more optimum postural positions. For purposes of this specification, a module may be implemented as a hardware circuit comprising custom VLSI circuits or gate arrays, off-the-shelf semiconductors such as logic chips, transistors, or other discrete components. A module may also be implemented in programmable hardware devices such as field programmable arrays, programmable array logic, programmable logic devices, and the like. Modules may also be implemented in software for execution by various types of processors. An identified module of executable code may, for instance, comprise one or more physical or logical blocks of computer instructions, which may, for instance, be organized as an object procedure, or function. Nevertheless, the executables of an identified module need not be physically located together, but may comprise disparate instructions stored in different locations, which when joined logically together, may comprise the module and achieve the stated purpose for the module.

As used herein, the term "substantially" refers to the complete or nearly complete extent or degree of an action, characteristic, property, state, structure, item, or result. For example, in one embodiment, an object that is "substantially" located within a housing would mean that the object is either completely within a housing or nearly completely within a housing. The exact allowable degree of deviation from absolute completeness may in some cases depend on the specific context. However, generally speaking the nearness of completion will be so as to have the same overall result as if absolute and total completion were obtained. The use of "substantially" is also equally applicable when used in a negative connotation to refer to the complete or near complete lack of an action, characteristic, property, state, structure, item, or result.

As used herein, the terms "approximately" and "about" generally refer to a deviance of within 5% of the indicated number or range of numbers. In one embodiment, the term "approximately" and "about", refer to a deviance of between 0.0001-10% from the indicated number or range of numbers.

It will be appreciated that terms such as "front," "back," "top," "bottom," "side," "short," "long," "up," "down," and "below" used herein are merely for ease of description and refer to the orientation of the components as shown in the figures. It should be understood that any orientation of the components described herein is within the scope of the present disclosure.

FIG. 1 is an illustration of a front view of one embodiment of the sensor device for improving posture and deep breathing. As shown in FIG. 1, one embodiment of the sensor device 100 for improving posture may be device, wearable or otherwise positionable on a user, such that the device may be adapted to be worn or connected to the body of the user. The device 100 may comprise: a housing 116, one or more sensors 106, 117, 118, microphone 119, LED lights 111, speaker 112, power supply 120, a wireless connection device 125, and a memory unit 128.

The sensors 106, 117, 118 may comprise one or more axis-related accelerometers and one or more axis-related gyroscopes. The axis-related accelerometers may be primary sensors configured to measure slower movements of the user. The axis-related gyroscopes may be sensors configured to measure quick or exaggerated changes in the position of the user. Additionally, in other embodiments, the sensors 106, 117, 118 may further comprise a pedometer, magnometer, thermometer, respiration rate meter, heart rate meter, blood pressure meter, light level meter, and/or global positioning system. In one embodiment, the accelerometers and gyroscopes may be configured to function as a pedometer, which may inform the system that the user is walking and amount of distance traveled.

The magnometer may be configured to detect the orientation of the user, the thermometer may be configured to determine both the ambient temperature and body temperature of the user, and the global positioning system may be configured to determine the physical location of the user. When multiple types of sensors are used, information gathered by the sensors may help determine multiple characteristics of the user such as his or her weight, height, pressure, orientation, heart rate, blood pressure, and respiration rate. The sensors 106, 117, 118 may allow the system to detect any movement by the user, including breathing, deep breathing, forward, back, and/or side tilts, twisting, turning, bending, head position, and body alignment.

In a preferred embodiment, the device 100 may have three tri-axial accelerometers and three tri-axial gyroscopes. Preferably, all six sensors may be used for calibration of the system, setting the optimum postural positions (OPP) of the user, and monitoring user adherence to the OPP.

Preferably, the device 100 communicates and interfaces with an electronic data processing unit, sometimes referred to as user devices, in order for the data generated by the sensors 106, 117, 118 to be displayed to the user in an efficient and user-friendly manner.

In one embodiment, the device 100 may communicate with the user devices via a low power point-to-point communication protocol such as Bluetooth®. In other embodiments, the device may also communicate via other various protocols and technologies such as WiFi®, WiMax®, iBeacon®, near field communication (NFC) protocol, and Miracast®. In other embodiments, the device 100 may connect in a wired manner to the user devices. The wireless connection device 125 may be a transmitter, receiver, and or transceiver that communicates in any wireless manner with another electronic device.

The power supply 120 may be a battery. In various embodiments, however, the power supply 120 may also comprise an additional power source, such as alternating current electrically coupled to the sensor device 100.

The memory unit 128 may be used to capture or store data when the device 100 is not connected to a user device. In this manner, the data may be later transmitted and displayed to the user, including whether the user was able maintain his/her OPP. The sensor device or user device may each house memory and process data.

In addition to sensors 106, 117, 118, the device may also have the speaker 112, which may sound an audible alarm if the user remains out of OPP for too long, or to provide other alerts and communicative chirps to the user. The microphone 119 may act as another sensor that may be used, for example, to determine if the user is properly breathing or to intake verbal commands. The lights 111, which are preferably LED, but may be LCD or other forms of illumination, may provide the user with visual alerts or the status of the power supply (charging, needs to be charged, on, off, etc.).

Although FIG. 1 shows that the device 100 may be round or disc-shaped, the device 100 may be any shape.

FIG. 2 is an illustration of a side view of one embodiment of the sensor device. FIG. 3 is an illustration of a rear view of one embodiment of the sensor device. As shown in FIGS. 2 and 3, the device 100, or more particularly, the housing the device 100, may have a concave slope 199, a connection groove 198, a copper coil 197, and a flat end 201. The copper coil 197 may allow the user to charge the power supply by touchless induction or indirect conduction. In this manner, the device 100 may not need to feature a plug or a receptacle to attach to a charging cord. The device 100 may be placed on a charging cradle and the copper coil 197 allows the device 100 to charge the power supply 120. The copper coil 197, which may be designed to face the body of a user, may also act as a shield that prevents electromagnetic radiation from passing from the device 100 to the wearer. Finally, the copper coil 197 may also direct the wireless signals away from the user and out of the front of the device 100, which may improve the wireless connection between the device and any companion or synched user devices. The flat end 201 may be at the end of the concave slope 199. The flat end 201 may be configured to rest against the body of a user. Movement of the user may cause the device 100 to roll towards the sloped side 199, which may allow the device to be very sensitive to movement, even slight movements. This sensitivity may be beneficial in determining when the user is maintaining proper balance and whether the user is breathing correctly.

FIGS. 4A-C are illustrations of one embodiment of the deep breathing and posture improvement system interface.

As shown in FIG. 4A, one embodiment of the breathing and posture improvement system interface 400 may be displayed on the display screen of a user device. In this manner the user may receive real time warnings and updates from the posture and deep breathing improvement device 100. Although FIGS. 4A and 4B show the user device 100 as a LED display screen or monitor that might be part of a smart phone, laptop computer, or computer, the user device may be other computing devices, such as a smart watch, a keyboard, a mouse, eyewear, a tablet, a chair, a monitor, a smart television, or some other device that is used or worn by a user.

FIG. 4A shows that the posture and/or breathing improvement system may comprise a user device 400, which operates and displays a posture improvement system interface 420. The system interface 420 may comprise an OPP layout 425, which, as shown, may be an outline of a top plan view of a pictograph of a human. Other OPP layouts may be a bullseye, target, concentric circles, or a different pictograph, which may be relevant such as a spine that a user tries to keep in an optimum graphical shape. The system interface 420 may also comprise a posture target ball 430, which is shown as a ball, but may be any shape. For purposes of this disclosure the terms pictograph, bullseye, and target may mean the same thing. In various embodiments, the posture improvement system may be a software application running on the user device 400 that interfaces wirelessly with the device 100 in order to determine whether the user is maintaining his/her OPP. The system interface 420 may be displayed in the background or foreground of the display screen of the user device 400. When in the foreground, the system interface 420 may overlap another program. Although system interface 420 is shown as a human pictograph target 425 and posture target ball 430, it should be understood that other shapes or graphics could be used, so long as the user is provided with information regarding the maintenance of his/her OPP. FIG. 4B shows that the posture ball 430 is on the edge of the pictograph target 425, which means the user is failing to maintain the OPP. The system interface 420 may display the time 403 and the user's heart rate 402, which is preferably gathered from the device 100.

FIG. 4A also shows that the system interface 420 may comprise menus, including dashboard 605, settings 610, pause 620, and calibrate 630. When a user clicks on 430, 605, 610, 620, 630, they may expand to allow a user to interact with the system interface 420. Clicking on the ball 430 brings up the heads-up-display (HUD).

One embodiment of the system may require that the user take a periodic activity break. In one embodiment, the user is required to stretch in various directions. The target of system interface may be overlaid with a crosshair. The system may then require that the user move the posture target ball within the crosshair. This may be performed by having the user stretch to the right, back, left, and forward, which concurrently moves the posture target ball in the correct direction within the crosshair. This gamification of taking a break may prompt the user to actually comply with the request of taking an activity break. The periodic activity reminders may be set for any period, including, but not limited to, once every ten minutes, once every twenty minutes, once every thirty minutes, once an hour, and the like. In other embodiments, the user may be required to follow the ball to get to the target exercise or stretch position.

FIG. 4C is an illustration of one embodiment of the calibrate screen when the user clicks on or otherwise selects calibrate button 630. The first part of the calibration may be to have the user take some mindful breaths.

FIG. 5 is an illustration of another embodiment of the posture improvement system interface and shows pop up interface windows. As shown in FIG. 5, one embodiment of the system interface 480 may comprise an OPP layout 481, a posture target ball 482, an instructions screen 483, a warning settings screen 485, a devices screen 483, and an OPP settings screen 487.

In one embodiment, the instructions screen 483 may be positioned to the right of the system interface 480 and may provide instructions for calibrating and using the posture system. The instructions may be provided in any form, including text, videos, graphics, flow charts, and/or pictures. The instructions screen 483 or another screen that is part of the software program may allow the user to set up and/or calibrate the posture system. Preferably, the set up and calibration may be accomplished through a decision tree or wizard that takes the user step-by-step through the process. In one embodiment, the system may prompt the user to input basic information such as his or her height and weight. The user may also input information regarding any pain the user may be experiencing. Upon receiving the information from the user, the software program may prompt the user to place the device in the proper position. In an additional embodiment, the software program may provide the user with textual, pictorial, or video instructions 483 in order to further guide the user to the proper position for the device.

The warning settings screen 485 may allow the user to set and change the warnings used by the system interface 480 for notifying the user when he/she is not in OPP. For example, in one embodiment, the user may first select the appropriate device for setting the warnings. The presentation of devices may be related to the devices screen 486. Once a device is selected, such as a phone, as shown in FIG. 5, the user may then select how the phone will warn the user of misalignment or when the user is not in his/her OPP. In various embodiments, the user may choose to be notified or warned via sound notification, change in color, flash of light or change in brightness, vibration, current or shock, other type of sensory warning, or a change in the functionality of the device. Preferably, the user sets the warnings for each device loaded in the devices screen. All warnings may be adjustable. For example, the volume of the sound warning may also be adjustable, and the brightness of the flash of light may also be adjustable. Additional colors may be selected. The strength of the vibration may be adjustable.

The devices screen 486 may allow a user to select those user devices that will communicate with the sensor device. The user devices may include, but are not limited to: a smart phone, laptop computer, a smart watch, a keyboard, a mouse, a tablet, a chair, a monitor, eyewear, a smart television, or some other device that is used or worn by a user. In some embodiments, there is no real-time user device, and the warnings are provided directly by the sensor device. In this manner, the sensor device may directly warn the user via sound, light, touch (poke), vibration, and/or click. The sensor device may include an integrated additional device that provides such a warning, or one of the existing portions of the sensor device may provide the warning.

The OPP settings screen 487 may allow the user to select one or more positions to associate with an OPP. The positions are various seated, standing, and active positions, including, but are not limited to: watching media (including, but not limited to, phone, tablet, television, and virtual reality imaging); sport/activity (including, but not limited to, walking, running, cycling, golf, baseball, basketball, yoga, snowboarding, skiing, and football); driving; working, including, but not limited to, telephone, computer, and stand up desk); hospital bed/bed ridden; travel (airplane travel); interactive games (computer and board games); presentations; personal confidence; repetitive occupational motion; specific occupational needs. Once the OPP settings are inputted into the system, the user may then calibrate each of the OPP by donning the sensor device and assuming the approximate correct position.

Once the posture improvement system is calibrated and set up, the user may use the system to ensure that the OPP is maintained during use. This is done by activating and donning the sensor device. The user must also select a user device and open the system interface 480 on that device. The system interface 480 may then inform the user whether his/her OPP is being maintained.

In one embodiment, the system interface 480 may alert the user to take periodic activity breaks, such as standing and/or stretching. The system interface 480 may also suggest a particular activity for the user to engage in during the activity break based on information regarding user pain and user conformance to his/her OPP.

Preferably, the user may switch from one OPP to another. This switch may be manually inputted by the user, thereby informing the system of the change. The switch may also be automatic, such that the device determines that the user has switched positions and intuitively changes to the more correct and appropriate OPP. This automatic switch preferably allows the user to confirm or reject the automatic switch. Regarding the automatic switch, in one embodiment, the system includes: a sensor device; and a posture improvement software program installed on multiple user devices, which possesses a notification system of OPP and an OPP display. This embodiment highlights the need for a smart and seamless network recognition system of the multiple user devices, such that the user is notified only on the appropriate user device. The description of "appropriate user device" in this embodiment is described by: proximity to other user devices, level and or the activity of the user, and user devices in use. In one example, where the seamless networking recognition system utilizes proximity as the primary factor for user device selection, a user working at a computer will have the posture improvement software displayed on the computer screen. Once the user discontinues work and leaves the proximity of the computer, the posture improvement software may no longer be required to be running on the computer. The sensor device seamlessly transitions the posture improvement software system to display on the next appropriate user device. This user device may be a smart phone, a tablet computer, a smart watch, other wearable devices, or other suitable device for OPP notification display or activity. Furthermore, the sensor device or the user device may relay information regarding active use of specific user devices as a mechanism for seamless network sensing (i.e. proximity to a computer workstation and/or the user is engaged in active use of a smart phone for an extended period, therefore, the posture improvement software displays on the smart phone). In another example, where a user chooses to engage in exercise by running, the activity level and pattern of movement detected by the sensor device will select a smart watch as the most appropriate user device, as opposed to a smart phone. In addition to these examples, a hybrid model that utilizes both proximity and activity may also be used to determine the appropriate device in which to activate the interface. In various embodiments, seamless switching between devices may be performed either automatically by the sensor, or manually selected by the user. In addition, seamless switching determination may be performed by the sensor device, or the user devices.

In various embodiments, the one or more accelerometers sense and determine the posture of the user, determine when the user takes a step, when a user takes a breath, and whether the breath is diaphragmatic. The gyroscope contributes data to the determination of the posture of the user, detecting twisting movements, and the determination as to whether the breath is diaphragmatic. In some embodiments, the user may manually set on the device or system where on the body the device will be worn (front, back, belly, neck, etc.). In other embodiments, the system may be programed to automatically detect and determine where on the body the device is placed and, if the device is moved to a different body part, the device may determine this and switch its functionality to working with the new placement on the body. In some embodiments, the heart rate monitor may be turned off or the system may remove it from the display. Turning it off may allow the battery in the device to work longer. The thermometer may display in Celsius, Fahrenheit, or both.

FIGS. 6A-C are illustrations of one embodiment of the posture and deep breathing improvement system interface. FIGS. 6A-C shows the breathing kinetic graphical user interface 500 that may be shown on the display of the user device. The interface 500 may comprise a kinetic display 510, which may comprise optimal breath inhale graphic 515 and actual dynamic kinetic breathing graphic 520, 521, 522. FIG. 6A shows that the user has inhaled a diaphragmatic breath, which is mirrored on the display 510 as the actual dynamic kinetic breathing graphic 520 expanded to at or approximately at the optimal breath inhale graphic. FIG. 6B shows that the user is exhaling in a diaphragmatic breath, which is shown by the actual dynamic kinetic breathing graphic 521 contracting 530. FIG. 6C shows that the user is inhaling in a diaphragmatic breath, which is shown by the actual dynamic kinetic breathing graphic 522 expanding 535. The breathing interface preferably allows a user to monitor his/her diaphragmatic breathing by watching the actual dynamic kinetic breathing graphic 520, 521, 522 expand and contract. The expansion of the actual dynamic kinetic breathing graphic 520, 521, 522 may optimally peak at the optimal breath inhale graphic 515, which is set by the system or the user. Although the actual dynamic kinetic breathing graphic 520, 521, 522 and the optimal breath inhale graphic 515 are shown as a circle and a dilating (telescopically expanding and contracting) dot (or ball), any kinetic graphical user interface or display may be used, so long as it translates the user's actual diaphragmatic breaths to a dynamic display that is visible to the user. In some embodiments, the kinetic breathing graphics may be shown as three-dimensional objects, such as spheres or dynamic kinetic sculptures.

The display 510 may also comprise an exhale graphic, which may be a circle that is smaller in diameter than the optimal breath inhale graphic 515 or it may be the disappearance (contracting into nothing) of the actual dynamic kinetic breathing graphic 520, 521, 522.

When the user is able to track his/her diaphragmatic breathing, the user is trained to take the optimal diaphragmatic breaths, which may significantly improve the physical and mental health of the user.

FIG. 7 is an illustration of another embodiment of the posture and deep breathing improvement system interface. As shown in FIG. 7, the interface 650 may comprise an ideal breath guide ring 651, which dilates in and out and acts as an ideal guide to the actual user breath ball 652, which is a depiction of the user's actual breathing as measured by the device. In this embodiment the user may be guided to make an ideal breath, inhale and exhale, or multiple ideal breaths.

FIG. 8 is an illustration of another embodiment of the posture and deep breathing improvement system interface. As shown in FIG. 8, the interface 660 may comprise an ideal breath guide ring 661, which dilates in and out and acts as an ideal guide to the actual user breath ball 662, which is a depiction of the user's actual breathing as measured by the device. In this embodiment the user may be guided to make an ideal breath, inhale and exhale, or multiple ideal breaths. The interface 660 may also comprise breath instructions 665, current heart rate 664, time left in the breathing session 667, and session graphic 669, which shows the number of cycles in the session and how many sessions have been completed. Session progress graphic 669 shows that the first of three sessions have been completed. FIG. 8 also shows that the interface may have a cycle time meter 670 that may comprise inhale 671, hold 672, exhale 673, and hold 674. The interface 660 may lead the user through a series of optimal deep breaths, which provides timing information 667, dynamic kinetic display 661, 662, cycle meter 670, and session progress 669.

FIG. 9 is an illustration of another embodiment of the posture and deep breathing improvement system interface and shows the settings screen. As shown in FIG. 9, when the user clicks on or otherwise selects the setting button 903 on interface 900, the user has may be presented with options, including mute/unmute 908, vibrate/no vibrate 906, quick settings 910, and OPP setting 904.

FIG. 10 is an illustration of another embodiment of the posture and deep breathing improvement system interface and shows the pause screen. When the user clicks on the pause icon or button 1001 of interface 1000, the system may pause. When the system is paused, the pause icon 1001 may become a play icon 1001, which when clicked, may start the system.

FIG. 11 is an illustration of another embodiment of the posture and deep breathing improvement system interface and shows the dashboard screen. When the user selects dashboard icon 605 on interface 400, dashboard 1100 may be pulled up. As shown in FIG. 11, the dashboard may comprise detailed information about the use of the sensor device and is a way the user may track their progress. The dashboard 1100 may have summary displays and various widgets that provide the user with information and graphs via a graphical user interface. The dashboard 1100 may comprise summary display 1101, which may comprise a greeting, rewards (Pats), user profile/avatar, wear time, weight graphic, heart rate tracking, active time, step count, percentage of time spent in OPP (good posture), Me/Mo, and the OPP interface. The dashboard 1100 may also comprise progress tracking 1102, posture report 1103, Me Moment (Me/Mo) details 1104, heart rate 1105, steps 1106, new messages 1110, input interface 1112 (which may allow the user to input data, such as body weight, mass, or body mass index), current challenge 1114, breath challenge 1116, link to view more challenges 1117, and dashboard tabs 1199.

FIG. 12 is an illustration of another embodiment of the posture and deep breathing improvement system interface and shows the HUD screen. When the user clicks on the posture ball 1430 of interface 1400, the HUD will pop up, which may comprise wear time 1440, steps 1441, posture report 1442, weight 1443, rewards 1444, temperature 1445, Me/Mo 1446, and user status 1447 (which may be shown as an emoji). When the user releases the click, or re-clicks, on the ball 1430, the HUD may retract or go away.

FIG. 13 is an illustration of another embodiment of the posture and deep breathing improvement system interface and shows the Me/Mo screen 1650. The Me/Mo screen 1650 may pop-up and suggest that user take a personal moment for a stretch break or a breathing break 1651. The user may start this by clicking on start 1652. As shown in FIG. 11, the Me/Mo moments may be measured and tracked.

FIG. 14 is an illustration of another embodiment of the posture and deep breathing improvement system interface and shows the dashboard settings screen. As shown in FIG. 14, the user may select settings in the dashboard tab 1199, which pulls up the OPP settings 1150 and the devices/device locations 1151. The dashboard summary 1101 may remain on the dashboard display 1100. This may allow the user to manually set the OPP (walking, sitting, standing, working, driving, playing, piano, and the like).

FIG. 15 is an illustration of one embodiment of a holder and harness for the sensor device. FIG. 15 shows that the device 100 may be configured to be cradled by holder 635 at the side groove 198 of device 100. Holder 635 may be configured to permanently or removeably hold the posture and breathing device 100. The holder 635 may be connected, permanently or removeably, to a harness 610, which may be configured to be worn by a user. The harness 610 preferably may hold the device 100 next to the user in one of several specific placements so as to detect and determine the user's posture, breathing, heart rate, etc. The holder 635 and harness 610 may be connected by a hinge, such as a ball and socket, that allows free range of motion of the holder 635. The harness 610 may be rigid, flexible, fixed, adjustable, or poseable, so long as it places and generally holds in place the device in proper proximity to the user.

When the harness and holder is used to hold the device in the proper position, the device may sense and measure almost any movement of the user, including head tilting, bending, twisting, turning, standing, sitting, walking, riding, biking, running, and stretching. Preferably, the harness may be bendable, flexible, and/or, as preferred, poseable. In this manner, the user can contour the harness to his/her body structure for comfort and for maintaining the device in substantially the same place during use. In a preferred embodiment, the harness may be configured to maximize user comfort. The harness may comprise a comfortable plastic coating that houses a poseable and conforming wire (or many wires laid/wrapped/twisted in sequence) constructed of a shape-memory alloy. Shape-memory alloys, such as nickel titanium (NiTi), are also commonly referred to as SMA, smart metal, memory metal, memory alloy, muscle wire, or smart alloy. In this manner, the harness may be heated or electrically charged, put into a specific shape and then cooled or removed from the charge, such that the harness then holds this specific shape. Preferably, the device may be held in many different locations on the wearer.

FIG. 16 is an illustration of another embodiment of a holder for the sensor device. As shown in FIG. 16, one embodiment of the holder 700 may comprise a ring 710, mating protrusion 720, and connector 730. The ring 710 and mating protrusion 720 may be configured to matingly engage with a posture and breathing device, such that the posture and breathing device is held firmly and with the proper orientation by the holder 700.

FIG. 17 is an illustration of one embodiment of a poseable harness. The poseable harness 1500 may comprise a back portion 1504, front portion 1503, shoulder portion 1502, and ear buds (headphones) 1501. The poseable harness 1500 is configured to matingly and snuggly fit on the shoulders of the user in a comforting and soothing manner. The sensor device may be connected to the harness 1500 at the back dip 1505. FIG. 17 shows that the poseable harness 1500 may be constructed of a sheathed copper coil that provides additional copper related benefits to the user.

FIG. 18 is an illustration of one embodiment of a poseable harness showing retractable headphones. FIG. 18 shows that the user 1599 may don the harness 1600, which is shown without its sheath, in a manner that matingly conforms to the user's shoulders. The harness 1600 may have earbuds or headphones 1601, which have a retraction device 1602, which allows the earbuds to be used and then retractably put away. This allows the user to make dual use of the harness 1600: holding the sensor device appropriately and listening to audio entertainment.

Unless otherwise stated, all measurements, values, ratings, positions, magnitudes, sizes, locations, and other specifications that are set forth in this specification, including in the claims that follow, are approximate, not exact. They are intended to have a reasonable range that is consistent with the functions to which they relate and with what is customary in the art to which they pertain.

The foregoing description of the preferred embodiment has been presented for the purposes of illustration and description. While multiple embodiments are disclosed, still other embodiments will become apparent to those skilled in the art from the above detailed description, which shows and describes the illustrative embodiments. These embodiments are capable of modifications in various obvious aspects, all without departing from the spirit and scope of protection. Accordingly, the detailed description is to be regarded as illustrative in nature and not restrictive. Also, although not explicitly recited, one or more embodiments may be practiced in combination or conjunction with one another. Furthermore, the reference or non-reference to a particular embodiment shall not be interpreted to limit the scope of protection. It is intended that the scope not be limited by this detailed description, but by the claims and the equivalents to the claims that are appended hereto.

Except as stated immediately above, nothing that has been stated or illustrated is intended or should be interpreted to cause a dedication of any component, step, feature, object, benefit, advantage, or equivalent, to the public, regardless of whether it is or is not recited in the claims.

What is claimed is:

1. A system for improving posture and deep breathing, comprising:
    a sensor device;
    a posture and breathing improvement software program that is configured to run on one or more user devices;
    wherein said posture and breathing improvement software program comprises a breathing kinetic graphical user interface;
    wherein said breathing kinetic graphical user interface is displayed on said one or more user devices;
    wherein said breathing kinetic graphical user interface comprises an optimal breath inhale graphic and an actual dynamic kinetic breathing graphic;
    wherein said actual dynamic kinetic breathing graphic expands and contracts, such that a user is able to visually monitor diaphragmatic breathing;
    wherein said sensor device comprises one or more sensors;
    wherein said one or more sensors are configured to detect and measure one or more movements by said user to create a plurality of sensor data;
    wherein a detection, measurement, and transmission of said plurality of sensor data allows said one or more user devices to allow said user to monitor their diaphragmatic breathing;
    wherein said actual dynamic kinetic breathing graphic and said optimal breath inhale graphic are, respectively, a dilating dot and a circle; and
    wherein said optimal breath inhale graphic is an expansion goal for said actual dynamic kinetic breathing graphic.

2. A system for improving posture and deep breathing, comprising:
    a sensor device;
    a posture and breathing improvement software program that is configured to run on one or more user devices;
    wherein said posture and breathing improvement software program comprises a breathing kinetic graphical user interface;
    wherein said breathing kinetic graphical user interface is displayed on said one or more user devices;
    wherein said breathing kinetic graphical user interface comprises an optimal breath inhale graphic and an actual dynamic kinetic breathing graphic;
    wherein said actual dynamic kinetic breathing graphic expands and contracts, such that a user is able to visually monitor diaphragmatic breathing;
    wherein said sensor device comprises one or more sensors;
    wherein said one or more sensors are configured to detect and measure one or more movements by said user to create a plurality of sensor data; and
    wherein said optimal breath inhale graphic is a dynamic kinetic circle that dilates and is a goal that said user tries to matingly follow via said actual dynamic kinetic breathing graphic.

3. A system for improving posture and deep breathing, comprising:
    a sensor device;
    a posture and breathing improvement software program that is configured to run on one or more user devices;
    wherein said posture and breathing improvement software program comprises a breathing kinetic graphical user interface;
    wherein said breathing kinetic graphical user interface is displayed on said one or more user devices;
    wherein said breathing kinetic graphical user interface comprises an optimal breath inhale graphic and an actual dynamic kinetic breathing graphic;
    wherein said actual dynamic kinetic breathing graphic expands and contracts, such that a user is able to visually monitor diaphragmatic breathing;
    wherein said sensor device comprises one or more sensors;
    wherein said one or more sensors are configured to detect and measure one or more movements by said user to create a plurality of sensor data; and
    wherein said housing comprises a copper coil, wherein said copper coil is configured to allow said sensor device to be wirelessly recharged.

4. The system of claim 3, wherein said copper coil is configured to a) shield said user from electromagnetic radiation generated by said sensor device and b) direct wireless communications away from said user.

5. A system for improving posture and deep breathing, comprising:
    a sensor device;

a posture and breathing improvement software program that is configured to run on one or more user devices;

wherein said posture and breathing improvement software program comprises a breathing kinetic graphical user interface;

wherein said breathing kinetic graphical user interface is displayed on said one or more user devices;

wherein said breathing kinetic graphical user interface comprises an optimal breath inhale graphic and an actual dynamic kinetic breathing graphic;

wherein said actual dynamic kinetic breathing graphic expands and contracts, such that a user is able to visually monitor diaphragmatic breathing;

wherein said sensor device comprises one or more sensors;

wherein said one or more sensors are configured to detect and measure one or more movements by said user to create a plurality of sensor data;

wherein said posture and breathing improvement software program further comprises a posture improvement system interface;

wherein said posture improvement system interface is displayed to said user on said one or more user devices;

wherein said posture improvement software program is configured to collect information about said user;

wherein said posture and breathing improvement software program calculates one or more optimum postural positions for said user, based on data communicated by said sensor device and said collected information about said user.

6. The system of claim 5, wherein said posture and breathing improvement software program monitors a conformance of said user with at least one of said one or more optimum postural positions;

wherein said posture improvement system interface is configured to display said conformance; and wherein said posture and breathing improvement software program detects and notifies said user of one or more non-conformances, such that a user is reminded to maintain said at least one of said one or more optimum postural positions.

7. The system of claim 6, wherein said displaying of said conformance of said user with at least one of said one or more optimum postural positions is illustrated via a pictograph target and a target ball.

8. The system of claim 7, wherein said posture target ball is substantially within a center of said target when said user is in said conformance with said at least one of said one or more optimum postural positions.

9. The system of claim 8, wherein when said user fails to maintain said at least one of said one or more optimum postural positions, said posture target ball is not substantially within said center of said target and said posture improvement system interface notifies said user of said one or more non-conformances.

10. The system of claim 9, wherein when said user fails to maintain said at least one of said one or more optimum postural positions, said user device is substantially disabled until said user corrects said non-conformance.

11. The system of claim 10, wherein said sensor device further comprises a memory unit;

wherein said memory unit stores said plurality of sensor data.

12. The system of claim 11, wherein said one or more sensors comprise: one or more accelerometers and one or more gyroscopes.

13. The system of claim 12, wherein said one or more accelerometers comprise three tri-axial accelerometers and said one or more gyroscopes comprise three tri-axial rate gyroscopes.

* * * * *